US012207792B2

(12) United States Patent
Yamashita (10) Patent No.: US 12,207,792 B2
(45) Date of Patent: Jan. 28, 2025

(54) ENDOSCOPE HOOD AND ENDOSCOPE SYSTEM

(71) Applicant: OLYMPUS CORPORATION, Tokyo (JP)

(72) Inventor: Susumu Yamashita, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 825 days.

(21) Appl. No.: 17/320,827

(22) Filed: May 14, 2021

(65) Prior Publication Data

US 2021/0267436 A1 Sep. 2, 2021

Related U.S. Application Data

(63) Continuation of application No. PCT/JP2018/042694, filed on Nov. 19, 2018.

(51) Int. Cl.
*A61B 1/00* (2006.01)
*A61N 5/06* (2006.01)

(52) U.S. Cl.
CPC ...... *A61B 1/00137* (2013.01); *A61B 1/00055* (2013.01); *A61B 1/00096* (2013.01);
(Continued)

(58) Field of Classification Search
CPC .............. A61B 1/00055; A61B 1/0008; A61B 1/00089; A61B 1/00096; A61B 1/00101;
(Continued)

(56) References Cited

U.S. PATENT DOCUMENTS 4,436,087 A * 3/1984 Ouchi ............... A61M 25/0133
600/153
5,547,457 A * 8/1996 Tsuyuki ............. A61B 1/00096
600/175
(Continued)

FOREIGN PATENT DOCUMENTS

JP S63-136015 A 6/1988
JP H05-329094 A 12/1993
(Continued)

OTHER PUBLICATIONS

Japanese Office Action dated Jul. 26, 2022 received in 2020-557046.
(Continued)

*Primary Examiner* — Aaron B Fairchild
(74) *Attorney, Agent, or Firm* — Scully, Scott, Murphy & Presser, P.C.

(57) ABSTRACT

An endoscope hood is attached to an endoscope insertion section including an optical fiber that optically guides therapeutic light with which biological tissue is to be irradiated and outputs the therapeutic light, and including an observation optical system for observing the biological tissue. The hood includes: an attachment section attached to a distal end of the endoscope insertion section; a pressing section including a pressing surface that presses against the biological tissue, the therapeutic light output from the optical fiber being transmittable through the pressing section; a transmission section disposed forward of the observation optical system, light being transmittable through the transmission section toward the observation optical system; and a blocking member disposed between a position where the distal end of the optical fiber is disposed and the transmission section, the therapeutic light output from the optical fiber
(Continued)

being prevented from entering the transmission section by the blocking member.

20 Claims, 10 Drawing Sheets

(52) U.S. Cl.
CPC ........ *A61B 1/00165* (2013.01); *A61N 5/0603* (2013.01); *A61N 2005/063* (2013.01)

(58) Field of Classification Search
CPC ............ A61B 1/00105; A61B 1/00137; A61B 1/00165
See application file for complete search history.

(56) References Cited

U.S. PATENT DOCUMENTS

| 2005/0165462 | A1 | 7/2005 | Bays et al. |
| 2006/0184048 | A1 | 8/2006 | Saadat |
| 2007/0066870 | A1 | 3/2007 | Ohashi et al. |
| 2008/0262315 | A1* | 10/2008 | Inoue ................. A61B 1/00181 600/168 |
| 2009/0253966 | A1* | 10/2009 | Ichimura ............ A61B 1/00181 600/158 |
| 2012/0209074 | A1 | 8/2012 | Titus |
| 2015/0065795 | A1 | 3/2015 | Titus |
| 2020/0281448 | A1 | 9/2020 | Titus |
| 2021/0015347 | A1 | 1/2021 | Titus |

FOREIGN PATENT DOCUMENTS

| JP | 2006-507016 A | 3/2006 |
| JP | 2007-082767 A | 4/2007 |
| JP | 2008-528239 A | 7/2008 |
| JP | 2012-187334 A | 10/2012 |
| JP | 2012-239527 A | 12/2012 |
| JP | 2014-510577 A | 5/2014 |
| JP | 2015-150154 A | 8/2015 |
| JP | 2016-140574 A | 8/2016 |
| JP | 2016-214374 A | 12/2016 |
| WO | 2003/065880 A2 | 8/2003 |
| WO | 2006083794 A2 | 8/2006 |
| WO | 2012112755 A2 | 8/2012 |

OTHER PUBLICATIONS

International Search Report dated Feb. 19, 2019 issued in PCT/JP2018/042694.

* cited by examiner

ENDOSCOPE HOOD AND ENDOSCOPE SYSTEM

CROSS-REFERENCE TO RELATED APPLICATIONS

This is a continuation of International Application PCT/JP2018/042694 which is hereby incorporated by reference herein in its entirety.

TECHNICAL FIELD

The present invention relates to endoscope hoods and endoscope systems.

BACKGROUND ART

A known laser treatment device in the related art treats lesion tissue of a patient by radiating therapeutic light onto the lesion tissue (for example, see Patent Literature 1). In the laser treatment device described in Patent Literature 1, a cap having a convex lens at the distal end thereof is attached to the distal end of an optical fiber, and the distal end of the cap is oriented toward the lesion tissue of the patient. In this state, laser light optically guided from a light source by the optical fiber is output from the distal end of the optical fiber via the convex lens of the cap, so that the surface of the lesion tissue of the patient intersecting the longitudinal direction of the optical fiber is uniformly irradiated with the laser light.

CITATION LIST

Patent Literature

PTL 1

Japanese Unexamined Patent Application, Publication No. 2016-214374

SUMMARY OF INVENTION

An aspect of the present invention provides an endoscope hood attached to an endoscope insertion section including an optical fiber that optically guides therapeutic light with which biological tissue is to be irradiated and outputs the therapeutic light from a distal end, and also including an observation optical system for observing the biological tissue. The endoscope hood includes an attachment section attached to a distal end of the endoscope insertion section, a pressing section including a pressing surface that presses against the biological tissue, a light transmission section disposed forward of the observation optical system, and an internal light blocking member disposed between a position where the distal end of the optical fiber is disposed and the light transmission section. The therapeutic light output from the optical fiber is transmittable through the pressing section. Light is transmittable through the light transmission section toward the observation optical system. The therapeutic light output from the distal end of the optical fiber is prevented from entering the light transmission section by the internal light blocking member.

DESCRIPTION OF EMBODIMENTS

First Embodiment

An endoscope hood and an endoscope system according to a first embodiment of the present invention will be described below with reference to the drawings.

Figure 1:
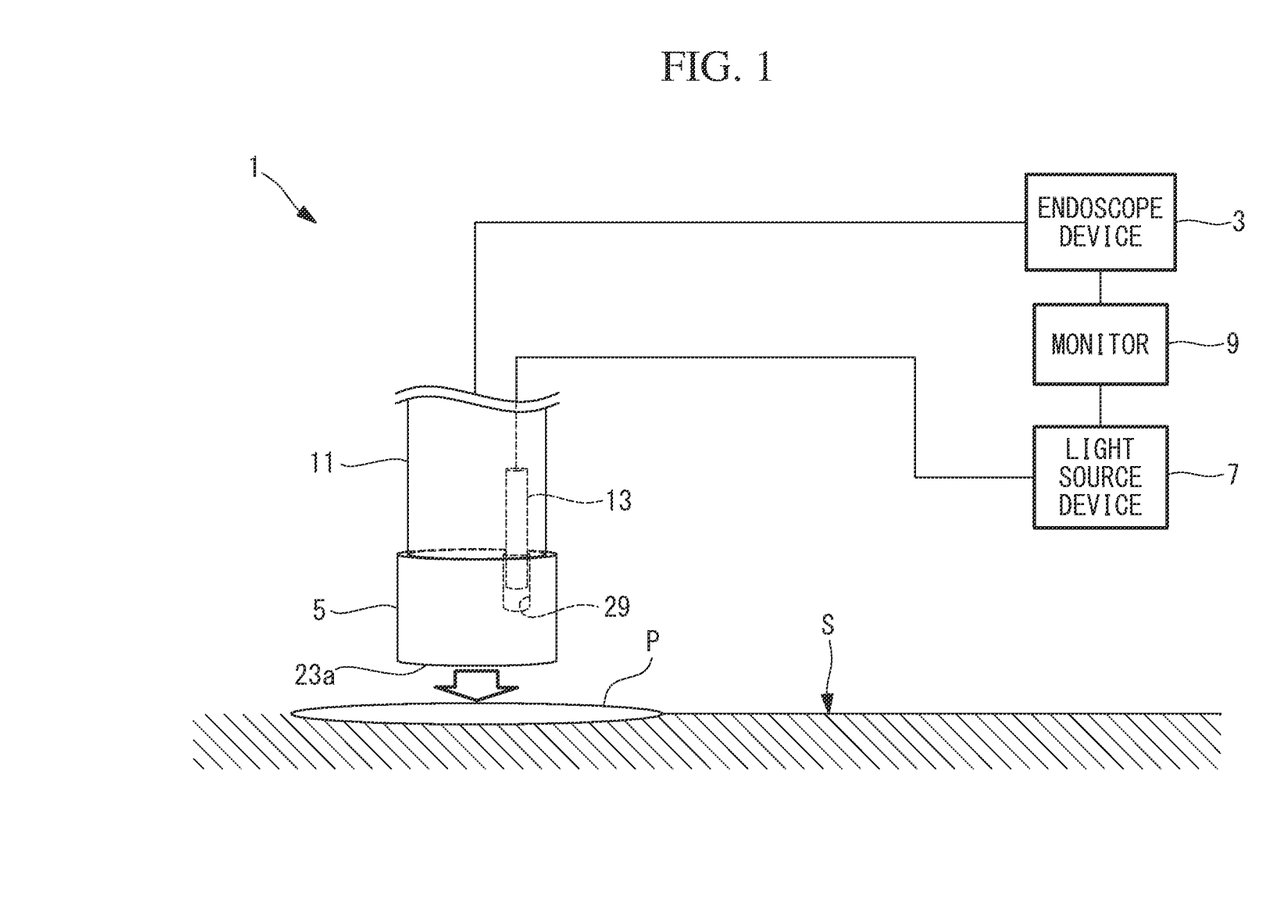
FIG. 1 schematically illustrates the configuration of an endoscope system according to a first embodiment of the present invention.

As shown in FIG. 1, an endoscope system 1 according to this embodiment includes an endoscope device 3, an endoscope hood 5 to be used together with the endoscope device 3, a light source device 7, and a monitor 9.

Figure 2:
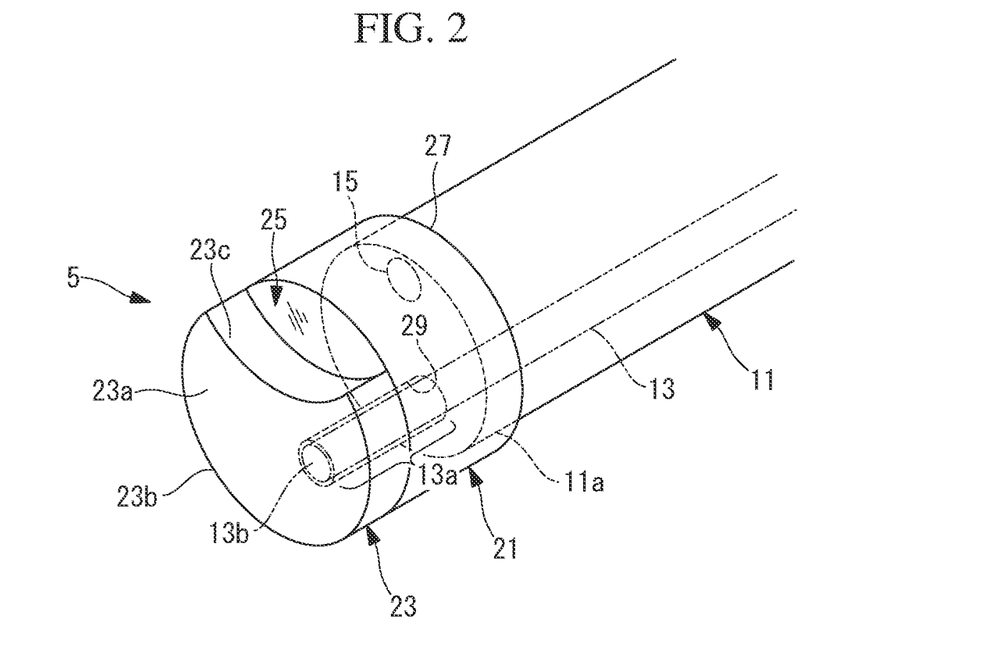
FIG. 2 is a perspective view of an endoscope insertion section and an endoscope hood in FIG. 1.
Figure 3:
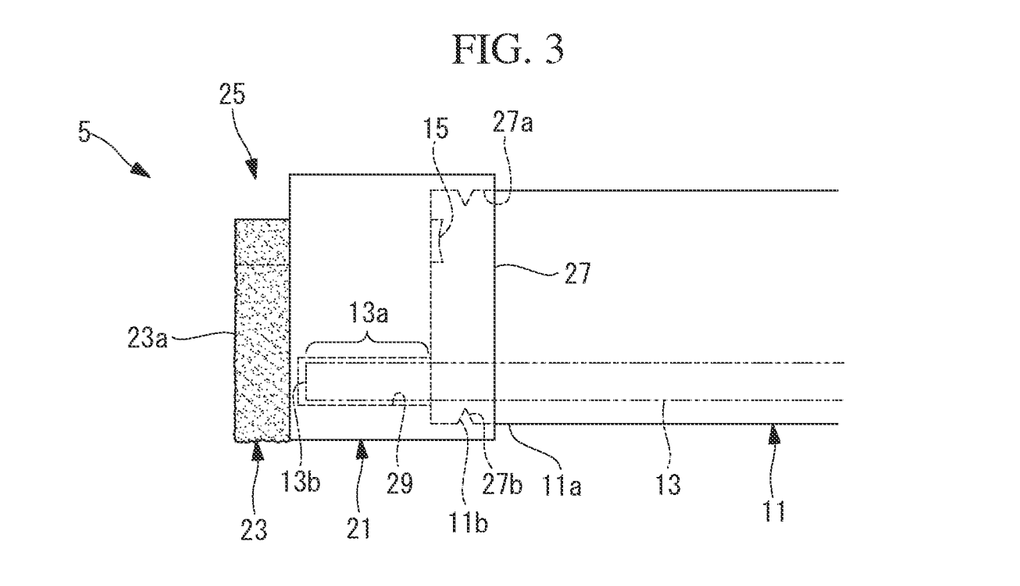
FIG. 3 is a side view of the endoscope insertion section and the endoscope hood in FIG. 1.

For example, as shown in FIGS. 2 and 3, the endoscope device 3 includes a long and narrow endoscope insertion section 11 to be inserted into a body cavity of a biological organism.

The endoscope insertion section 11 includes an optical fiber 13 that optically guides therapeutic light with which biological tissue S (see FIG. 1) is to be irradiated and outputs the therapeutic light from a distal end 13a, and also includes an observation optical system 15 for observing the biological tissue S. With regard to this endoscope insertion section 11, a distal end 11a thereof in the longitudinal direction is cylindrical.

For example, the optical fiber 13 is of a lateral radiating type and outputs therapeutic light from the side surface of the distal end 13a not including a distal end surface 13b. The therapeutic light output from the side surface of the distal end 13a expands radially so as to be also radiated forward of the distal end surface 13b.

Figure 4:
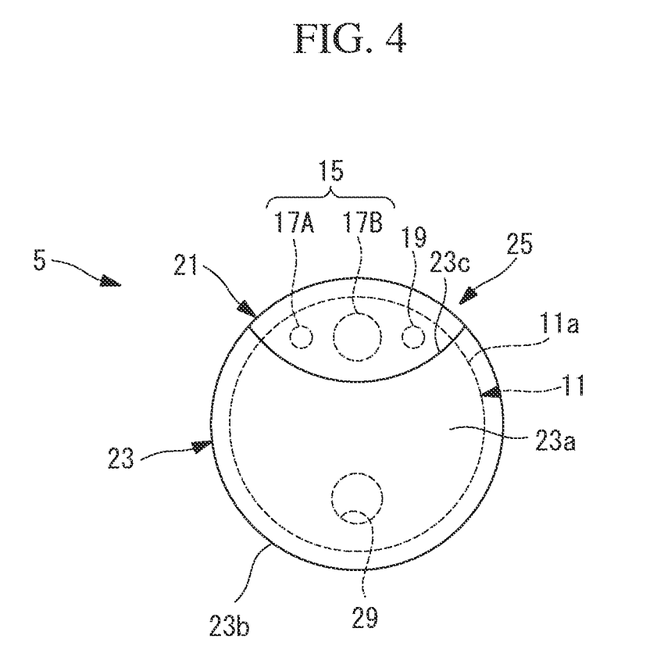
FIG. 4 is a front view of the endoscope insertion section and the endoscope hood in FIG. 1, as viewed from the side having a pressing surface in a direction parallel to a longitudinal axis of the endoscope insertion section.

For example, as shown in FIG. 4, the observation optical system 15 includes a reference light source (observation optical system) 17A that generates reference light to be output to the biological tissue S, and also includes a camera (observation optical system) 17B that captures an image of observation light from the biological tissue S. The reference light source 17A and the camera 17B are provided at the distal end 11*a* of the endoscope insertion section 11.

The distal end 11*a* is also provided with an air-water outlet 19 in the distal end surface thereof. The air-water outlet 19 can emit air and water onto the camera 17B so as to clean and remove, for example, blood and dust from the camera 17B. Furthermore, for example, as shown in FIG. 3, the distal end 11*a* is provided with a groove 11*b* that is recessed radially inward in the outer peripheral surface of the distal end 11*a*.

The monitor 9 displays an image of, for example, the biological tissue S captured by the camera 17B.

The light source device 7 generates therapeutic light for treating the biological tissue S to be treated, that is, a lesion P. The therapeutic light has a wavelength ranging between, for example, 650 nm and 750 nm. The therapeutic light emitted from the light source device 7 is optically guided by the optical fiber 13 and is subsequently output from the distal end 13*a* of the optical fiber 13.

As shown in FIGS. 2 and 3, the endoscope hood 5 includes a substantially cylindrical main body 21 disposed coaxially with the central axis of the endoscope insertion section 11, a pressing section 23 provided at the distal end of the main body 21, and a space section (light transmission section) 25 that is disposed in front of the observation optical system 15 and through which the observation light from the biological tissue S is transmittable.

The main body 21 is formed of a transparent component. The main body 21 has an attachment section 27 attached to the distal end 11*a* of the endoscope insertion section 11 and a fiber insertion hole 29 that extends toward the pressing section 23 from the attachment section 27 and into which the distal end 13*a* of the optical fiber 13 is insertable.

The attachment section 27 is provided at the proximal end of the main body 21 in the longitudinal direction. As shown in FIG. 3, the attachment section 27 has an engagement hole 27*a* that extends in the longitudinal direction of the main body 21 and that engages with the distal end 11*a* of the endoscope insertion section 11.

The engagement hole 27*a* has a claw 27*b* protruding radially inward from the inner peripheral surface thereof. In a state where the attachment section 27 of the endoscope hood 5 is attached to the distal end 11*a* of the endoscope insertion section 11, the claw 27*b* of the attachment section 27 is fitted in the groove 11*b* of the distal end 11*a*.

The fiber insertion hole 29 extends in the longitudinal direction of the main body 21 from the proximal end of the main body 21 to a position near the pressing section 23. Specifically, the fiber insertion hole 29 does not extend through the pressing section 23. Because the main body 21 is formed of a transparent component, when the optical fiber 13 is being inserted into the fiber insertion hole 29, the optical fiber 13 in the fiber insertion hole 29 can be viewed from outside the main body 21.

The pressing section 23 is formed of a component through which therapeutic light is transmittable. The pressing section 23 may be integrated with the main body 21 by using the same component as the main body 21, or may be independent from the main body 21 by using a different component from the main body 21.

Furthermore, the pressing section 23 has a pressing surface 23*a* disposed at a position where the pressing surface 23*a* covers at least the distal end surface 13*b* of the optical fiber 13. The pressing surface 23*a* is disposed orthogonally to the longitudinal direction of the main body 21. The fiber insertion hole 29 does not extend through the pressing surface 23*a*. Moreover, the pressing surface 23*a* is given, for example, an embossing treatment or a roughening treatment. Accordingly, this increases the friction between the pressing surface 23*a* and the biological tissue S against which the pressing surface 23*a* is pressed, whereby the pressing surface 23*a* can have a non-slip function. The pressing surface 23*a* may also have adhesiveness. Moreover, the edge of the pressing surface 23*a* may be chamfered.

The pressing section 23 protrudes forward from the distal end of the main body 21 and has a predetermined thickness, such as 3 mm to 10 mm. With this configuration, the pressing section 23 has sufficient durability for pressing against the biological tissue S, and can ensure a reasonable distance between the biological tissue S and the distal end surface 13*b* of the optical fiber 13 while pressing against the biological tissue S. Accordingly, based on the intensity of the therapeutic light, the advantages of light treatment can be exhibited, and treatment can be performed reasonably.

Furthermore, the pressing section 23 has a shape obtained by partially cutting out a disk that is centered on the central axis of the endoscope insertion section 11, that is, the central axis of the main body 21, and that has the same outer dimensions as the main body 21. In detail, as shown in FIGS. 2 and 4, the pressing section 23 and the pressing surface 23*a* thereof have a shape surrounded by a circular-arc-shaped first outer peripheral portion 23*b* serving as a part of the circumference around the central axis of the endoscope insertion section 11 and by a second outer peripheral portion 23*c* defined by the remaining part of the circumference being recessed radially inward into the shape of a circular arc.

The space section 25 is formed by the partially cut-out region of the disk centered on the central axis of the main body 21. The space section 25 causes the end surface of the region located forward of the observation optical system 15 and the air-water outlet 19 in the main body 21 to be exposed in a state where the end surface is recessed rearward relative to the pressing surface 23*a*. This configuration suppresses contact of the end surface of the region located forward of the observation optical system 15 and the air-water outlet 19 in the main body 21 with the biological tissue S when the pressing surface 23*a* is pressed against the biological tissue S, resulting in less soiling of the end surface.

The operation of the endoscope system 1 having the above-described configuration will now be described.

In order to perform light treatment on the lesion P in the biological tissue S by using the endoscope system 1 according to this embodiment, for example, a drug for treating the lesion P is injected into the biological tissue S in advance. Furthermore, as shown in FIGS. 2 and 3, in a state where the optical fiber 13 is inserted into the fiber insertion hole 29 in the endoscope hood 5, the attachment section 27 of the endoscope hood 5 is attached to the distal end 11*a* of the endoscope insertion section 11.

With the distal end 13*a* of the optical fiber 13 being inserted into the fiber insertion hole 29, the attachment section 27 is positioned in the circumferential direction of the endoscope insertion section 11. Accordingly, the pressing surface 23*a* of the pressing section 23 can be disposed at a position where the pressing surface 23*a* covers the distal end surface 13*b* of the optical fiber 13, and the endoscope hood 5 can be attached easily and accurately to the endoscope insertion section 11 in a position where the space section 25 is disposed forward of the observation optical system 15. Moreover, with the fiber insertion hole 29, a fixed distance can be maintained between the lesion P in the biological tissue S and the distal end surface 13b of the optical fiber 13.

Subsequently, the pressing surface 23a of the endoscope hood 5 attached to the endoscope insertion section 11 is disposed to face the lesion P. Then, reference light is output to the biological tissue S from the reference light source 17A, and an image of observation light from the biological tissue S is captured by the camera 17B, so that a user can check the position of the lesion P in the biological tissue S on the monitor 9.

Subsequently, as shown in FIG. 1, the pressing surface 23a of the endoscope hood 5 is pressed against the lesion P. In this state, therapeutic light is generated from the light source device 7, and the therapeutic light optically guided by the optical fiber 13 of the endoscope insertion section 11 is output from the distal end 13a of the optical fiber 13, so that the lesion P is irradiated with the therapeutic light via the pressing surface 23a of the pressing section 23.

Figure 5:
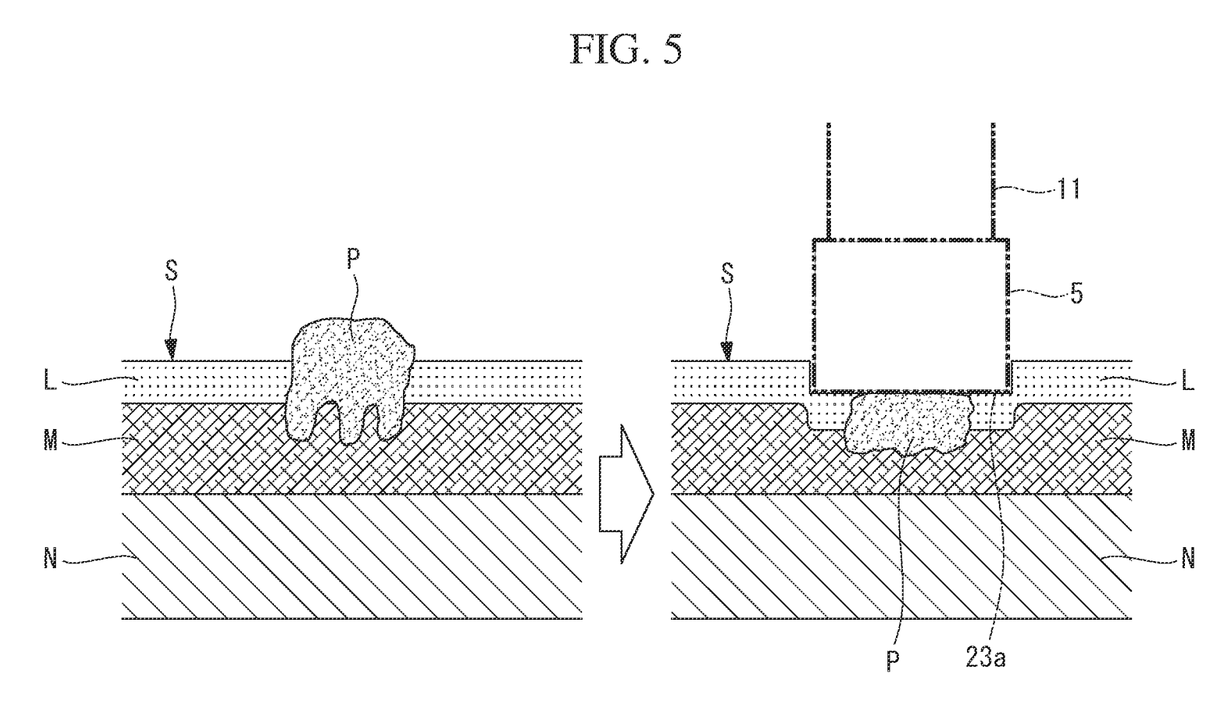
FIG. 5 illustrates how a lesion in biological tissue is pressed by the pressing surface of the endoscope hood.

In this case, the pressing surface 23a of the pressing section 23 is pressed against the lesion P, so that, for example, as shown in FIG. 5, the lesion P in the biological tissue S can be reduced in thickness and can have a nearly uniform thickness. Accordingly, by outputting the therapeutic light in this state, a deep part of the lesion P can be irradiated with a sufficient amount of therapeutic light more reliably. In FIG. 5, reference sign L denotes a mucous membrane, reference sign M denotes a submucosal layer, and reference sign N denotes a muscular layer.

As described above, in the endoscope system 1 and the endoscope hood 5 according to this embodiment, therapeutic light is radiated in a state where the endoscope hood 5 is attached to the endoscope insertion section 11 and the pressing surface 23a is pressed against the lesion P, so that a deep part of the lesion P can be irradiated with a sufficient amount of therapeutic light more reliably, whereby light treatment can be performed on the biological tissue S.

Furthermore, the embossing treatment or the roughening treatment performed on the pressing surface 23a increases the friction between the biological tissue S and the pressing surface 23a, so that the pressing section 23 is less likely to be positionally displaced relative to the biological tissue S in the state where the pressing surface 23a is pressed against the lesion P.

Furthermore, in a case where the endoscope hood 5 is attached to the endoscope insertion section 11 in an engaged state, the claw 27b of the attachment section 27 is fitted in the groove 11b of the endoscope insertion section 11, so that when the pressing surface 23a of the endoscope hood 5 is pressed against the biological tissue S, the endoscope hood 5 is less likely to become detached from the distal end 11a of the endoscope insertion section 11 even if pressure is applied to the endoscope hood 5 in a direction intersecting the longitudinal direction of the endoscope insertion section 11.

In this embodiment, for example, the curvature of the first outer peripheral portion 23b and the curvature of the second outer peripheral portion 23c in the pressing surface 23a may be equal to each other.

Figure 6:
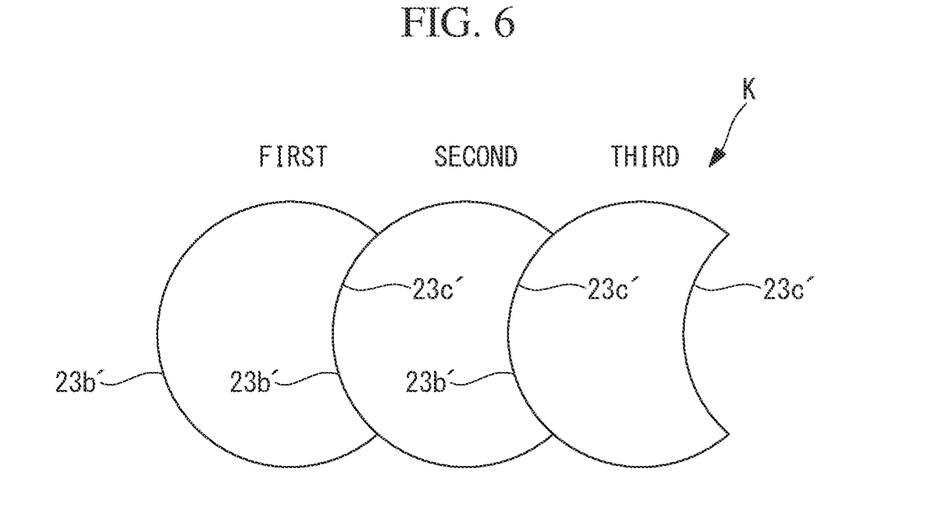
FIG. 6 illustrates an example of a continuous trace of the pressing surface in the biological tissue.

With this configuration, for example, in a case where the position where the pressing surface 23a is pressed against the biological tissue S is to be shifted sideways, as shown in FIG. 6, the first outer peripheral portion 23b of the pressing surface 23a is aligned with a position 23c' corresponding to the second outer peripheral portion 23c in a trace K of the pressing surface 23a in the biological tissue S, so that the shape at the position 23c' corresponding to the second outer peripheral portion 23c matches the shape at a position 23b' corresponding to the first outer peripheral portion 23b, whereby a gap between adjacent pressing locations can be reduced as much as possible.

Accordingly, in a case where the lesion P extends over a wide range and the therapeutic light has to be radiated a plurality of times while shifting the position, the biological tissue S is efficiently irradiated with the therapeutic light without waste while the pressing position of the pressing surface 23a is shifted sideways.

Figure 7:
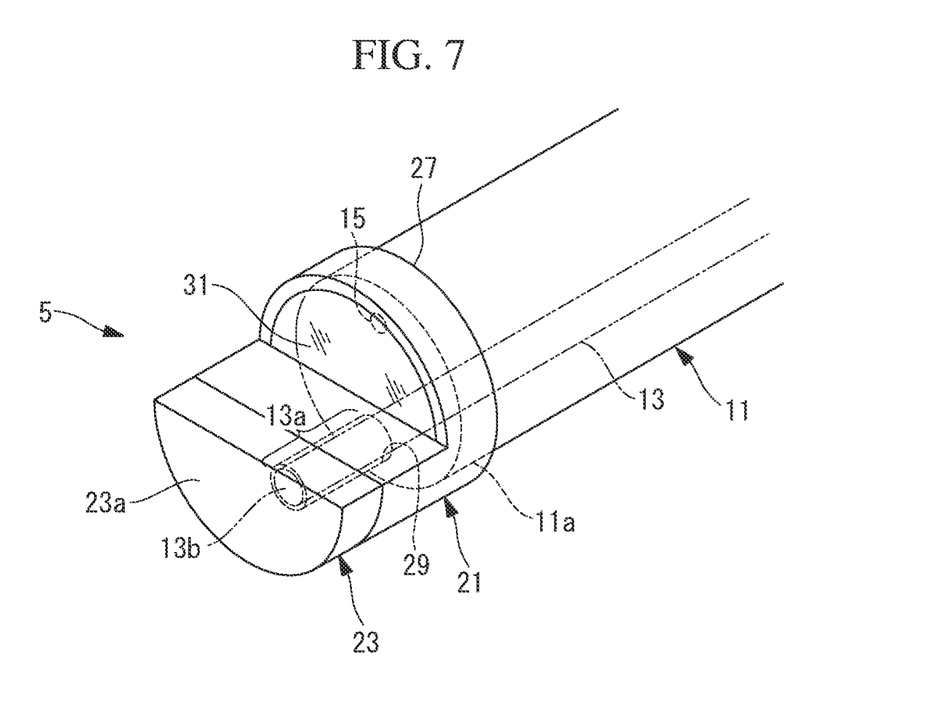
FIG. 7 is a perspective view of an endoscope hood according to a modification of the first embodiment of the present invention.

In this embodiment, the endoscope hood 5 has the space section 25. Alternatively, for example, as shown in FIG. 7, the space section 25 may be replaced with a transparent section 31 composed of a transparent material through which the observation light from the biological tissue S can pass toward the observation optical system 15.

With the space section 25 being changed to the transparent section 31, advantages similar to those in this embodiment can still be achieved.

Furthermore, this embodiment may be modified to the following configurations.

As a first modification, the pressing section 23 may be formed of a scattering element through which the therapeutic light is transmittable and that scatters the therapeutic light.

According to this configuration, the therapeutic light output from the distal end of the optical fiber 13 via the pressing section 23 can be scattered. Accordingly, the lesion P can be uniformly irradiated with the therapeutic light, so that the biological tissue S can be treated more efficiently over a wide range.

Figure 8:
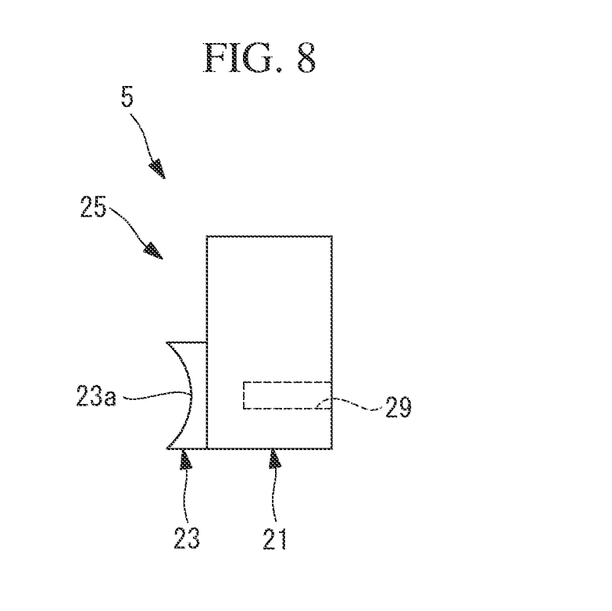
FIG. 8 is a side view of an endoscope hood in which the pressing surface has a recessed shape.

As a second modification, for example, as shown in FIG. 8, the pressing surface 23a of the pressing section 23 may have a recessed shape recessed rearward, that is, toward the endoscope insertion section 11.

According to this configuration, in a case where the surface of the lesion P has a protruding shape due to swelling of the lesion P, the pressing surface 23a of the pressing section 23 can be brought into close contact with the surface of the biological tissue S more easily.

Likewise, the pressing surface 23a of the pressing section 23 may have a protruding shape protruding forward, that is, toward the biological tissue S. For example, this is effective in a case where the surface of the lesion P has a recessed shape.

Figure 9:
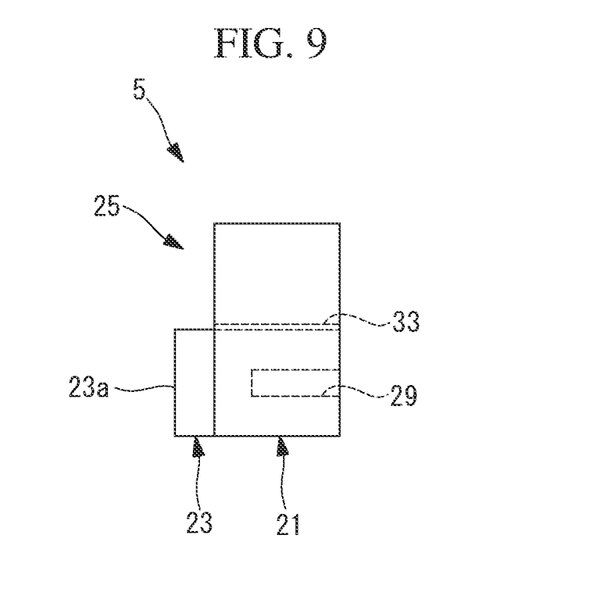
FIG. 9 is a side view of an endoscope hood having a light blocking member between a fiber insertion hole and a space section.

As a third modification, for example, as shown in FIG. 9, the endoscope hood 5 may include a light blocking member (internal light blocking member) 33 disposed between the fiber insertion hole 29 and the space section 25 or the transparent section 31.

The light blocking member 33 may be disposed between the position where the distal end 13a of the optical fiber 13 is disposed in the main body 21 and the space section 25 or the transparent section 31, and may be capable of blocking therapeutic light that is to enter the space section 25 or the transparent section 31 from the therapeutic light output from the distal end 13a of the optical fiber 13.

With this configuration, the light blocking member 33 can prevent the therapeutic light output from the distal end 13a of the optical fiber 13 in the endoscope insertion section 11 from entering the field of view of the endoscope device 3 via the space section 25 or the transparent section 31. Accordingly, the observation of the lesion P using the observation optical system 15 is prevented from being hindered by the therapeutic light, so that the lesion P can be observed while light treatment is being performed thereon.

Figure 10:
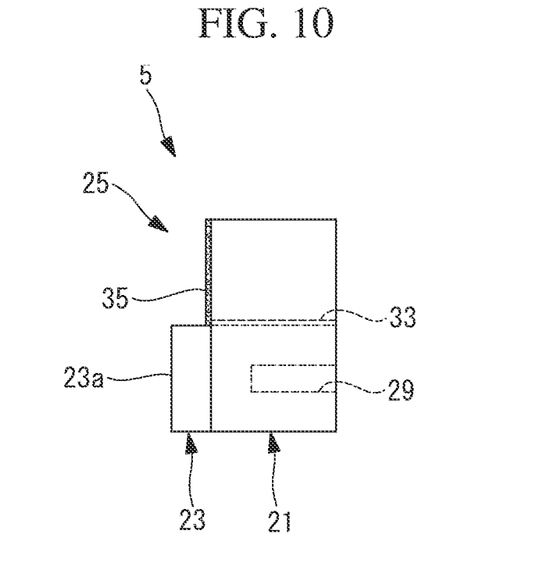
FIG. 10 is a side view of an endoscope hood having a light blocking member and a filter.

In this modification, for example, as shown in FIG. 10, the space section 25 or the transparent section 31 may include a filter (filter member) 35 that blocks therapeutic light incident thereon from the biological tissue S. For example, the filter 35 may be disposed at the end surface of the region located forward of the observation optical system 15 in the main body 21 of the endoscope hood 5.

According to this configuration, the filter 35 can prevent the therapeutic light output from the distal end 13a of the optical fiber 13 via the pressing surface 23a of the pressing section 23, coming in from the biological tissue S, and passing through the space section 25 or the transparent section 31 from entering the observation optical system 15. Accordingly, the biological tissue S can be observed more reliably and with higher accuracy while light treatment is being performed thereon.

Figure 11:
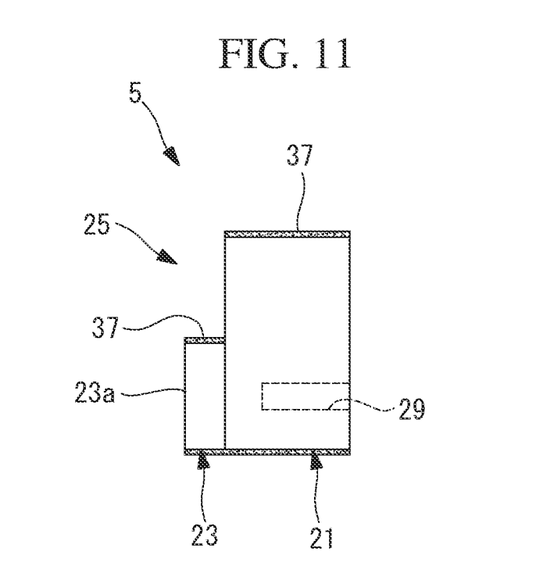
FIG. 11 is a side view of an endoscope hood having a light blocking member at a position where the light blocking member covers the side surface of the entire endoscope hood.

As a fourth modification, for example, as shown in FIG. 11, a light blocking member (external light blocking member) 37 that blocks therapeutic light may be disposed at a position where the light blocking member 37 covers the overall side surface including the pressing section 23 and the space section 25 or the transparent section 31, that is, the side surfaces of the pressing section 23 and the main body 21. The light blocking member 37 may be formed of, for example, a component that absorbs therapeutic light.

This configuration can prevent a portion of the therapeutic light output from the distal end 13a of the optical fiber 13 from being output outward from the overall side surface including the pressing section 23 and the space section 25 or the transparent section 31. Accordingly, areas other than the lesion P can be prevented from being irradiated with the therapeutic light.

Second Embodiment

Next, an endoscope system according to a second embodiment of the present invention will be described below with reference to the drawings.

Figure 12:
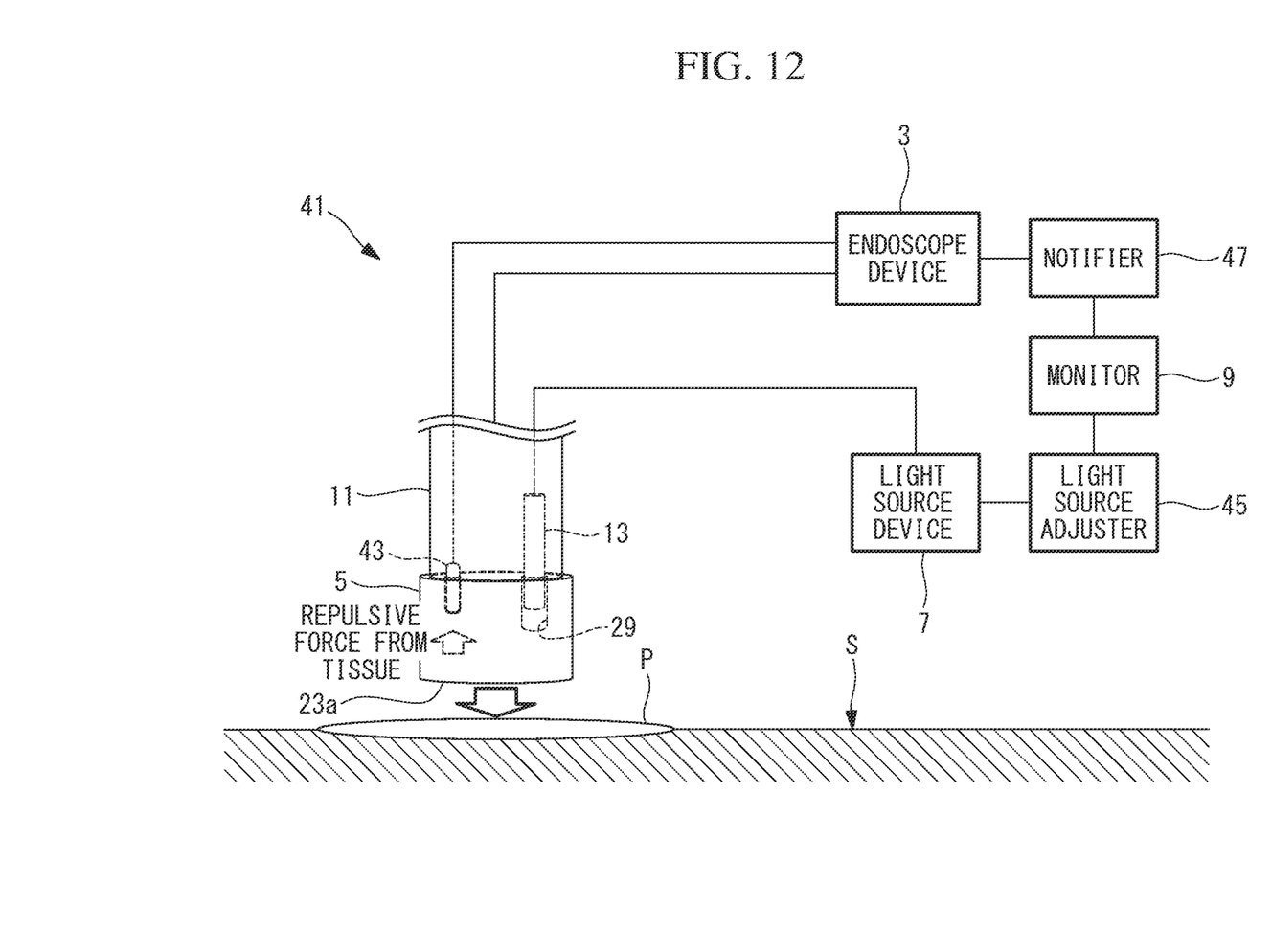
FIG. 12 schematically illustrates the configuration of an endoscope system according to a second embodiment of the present invention.

For example, as shown in FIG. 12, an endoscope system 41 according to this embodiment includes the endoscope device 3, the endoscope hood 5, a pressure sensor 43, the light source device 7, a light source adjuster 45, and a notifier (notification unit) 47.

In the description of this embodiment, components identical to those of the endoscope system 1 according to the first embodiment described above are given the same reference signs, and descriptions thereof are omitted.

The pressure sensor 43 is disposed in the endoscope hood 5. The pressure sensor 43 measures a contact pressure between the pressing surface 23a of the endoscope hood 5 and the biological tissue S, that is, a repulsive force from the biological tissue S to the pressing surface 23a. The repulsive force measured by the pressure sensor 43 is transmitted to the notifier 47.

The notifier 47 causes, for example, the monitor 9 to display information related to the repulsive force measured by the pressure sensor 43. In detail, the notifier 47 determines whether or not the repulsive force measured by the pressure sensor 43 is within an appropriate range, whether or not there is contact between the biological tissue S and the pressing surface 23a, and whether or not the biological tissue S is excessively pressed. Then, the notifier 47 causes the monitor 9 to display information based on the determination results.

In response to an operation performed by the user, the light source adjuster 45 can switch the irradiation mode of the therapeutic light from the light source device 7 between on and off modes and can adjust the intensity of therapeutic light to be generated from the light source device 7.

Figure 13:
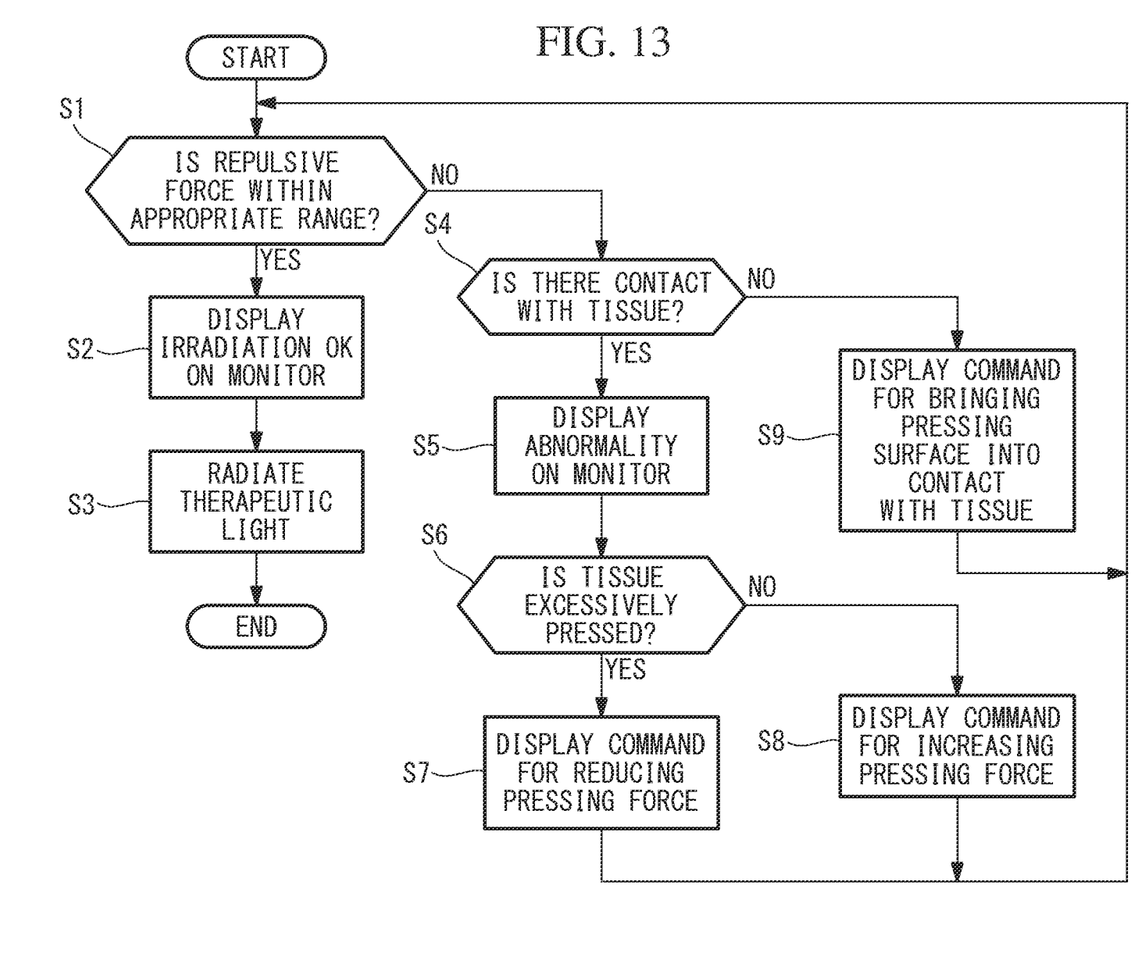
FIG. 13 is a flowchart illustrating the operation of the endoscope system according to the second embodiment of the present invention.

The operation of the endoscope system 41 having the above-described configuration will be described below with reference to a flowchart in FIG. 13.

In a case where light treatment is to be performed on the lesion P in the biological tissue S by using the endoscope system 41 according to this embodiment, the endoscope hood 5 is attached to the endoscope insertion section 11. When the pressing surface 23a of the endoscope hood 5 is pressed against the biological tissue S in this state, the repulsive force from the biological tissue S to the pressing surface 23a is measured by the pressure sensor 43. The measured repulsive force is transmitted from the pressure sensor 43 to the notifier 47.

The notifier 47 determines whether or not the repulsive force transmitted from the pressure sensor 43 is within an appropriate range (step S1). If it is determined that the repulsive force is within the appropriate range ("Yes" in step S1), the notifier 47 causes the monitor 9 to display the information "irradiation OK" (step S2). Accordingly, based on the display on the monitor 9, the user irradiates the lesion P with therapeutic light while checking the position of the lesion P (step S3).

In contrast, if it is determined that the repulsive force is not within the appropriate range ("No" in step S1), the notifier 47 determines whether or not there is contact between the pressing surface 23a and the biological tissue S (step S4). If it is determined that there is contact ("Yes" in step S4), the notifier 47 causes the monitor 9 to display the information "contact abnormality" (step S5).

Subsequently, the notifier 47 determines whether or not the repulsive force exceeds a predetermined threshold value, that is, whether or not the biological tissue S is excessively pressed (step S6). When the biological tissue S is excessively pressed, there is a possibility that the pressing section 23 may penetrate the biological tissue S. On the other hand, if the pressing force applied to the biological tissue S is insufficient, the lesion P in the biological tissue S cannot be sufficiently reduced in thickness.

If it is determined that the biological tissue S is excessively pressed, the notifier 47 causes the monitor 9 to display a command for "reducing the pressing force" (step S7), and the process returns to step S1. In contrast, if it is determined that the biological tissue S is not excessively pressed, the notifier 47 causes the monitor 9 to display a command for "increasing the pressing force" (step S8), and the process returns to step S1.

If it is determined in step S4 that there is no contact ("No" in step S4), the notifier 47 causes the monitor 9 to display a command for "bringing the pressing surface 23a into contact with the biological tissue S" (step S9), and the process returns to step S1.

As described above, in the endoscope system 41 according to this embodiment, the user can irradiate the biological tissue S with therapeutic light while ascertaining that the biological tissue S against which the pressing surface 23a of the pressing section 23 is pressed is reasonably thin and has a nearly uniform thickness based on the notification information provided by the notifier 47. Accordingly, a deep part of the biological tissue S can be irradiated with a sufficient amount of therapeutic light more reliably, so that the biological tissue S can be treated easily and efficiently.

As an alternative to this embodiment in which the notifier 47 causes the monitor 9 to display the information related to the repulsive force in text, for example, the notifier 47 may provide the notification about the information related to the repulsive force by using, for example, sound or color.

This embodiment may be modified to the following configurations.

Figure 14:
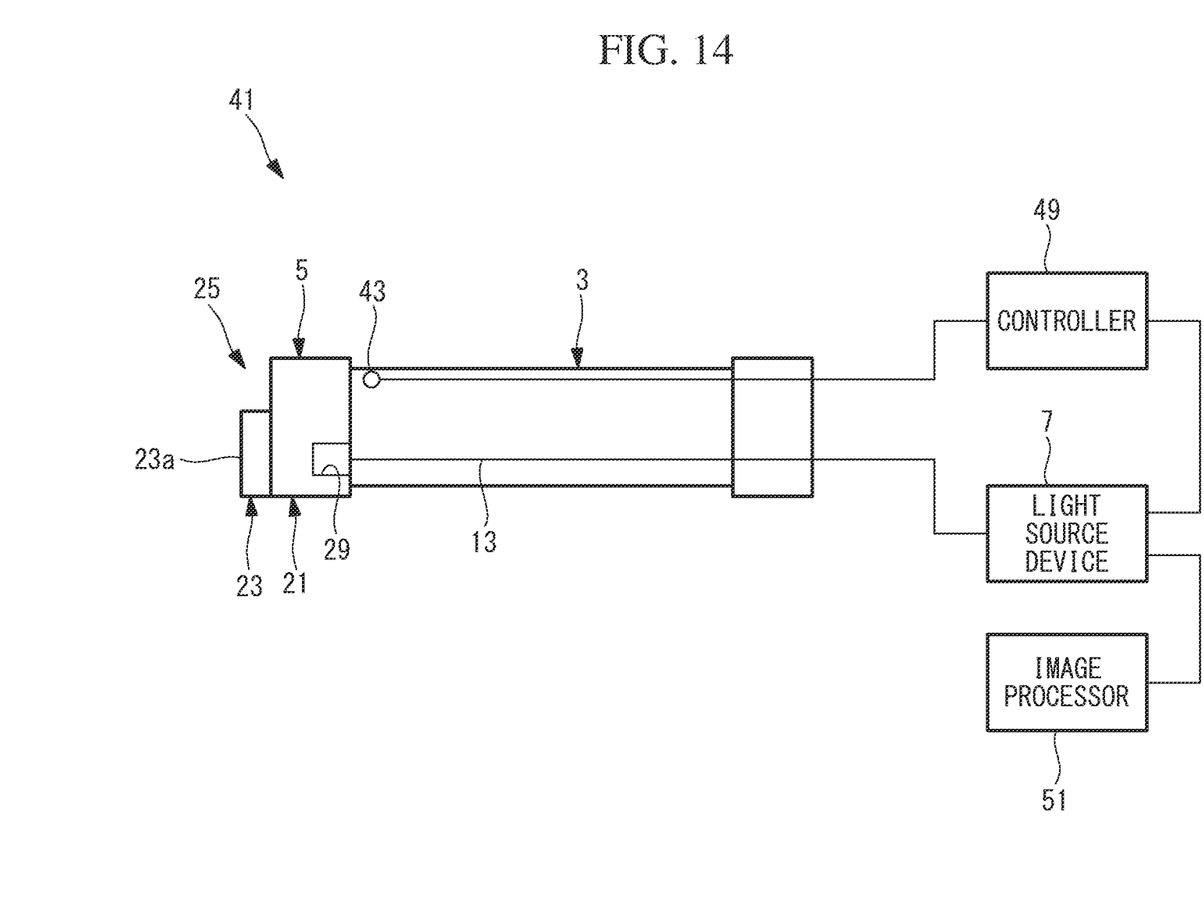
FIG. 14 schematically illustrates the configuration of an endoscope system according to a modification of the second embodiment of the present invention.

For example, as shown in FIG. 14, a controller 49 that controls the light source device 7 may be provided in place of the notifier 47, the monitor 9, and the light source adjuster 45. In FIG. 14, reference sign 51 denotes an image processor that processes an image acquired by the observation optical system 15.

The controller 49 determines whether or not the repulsive force measured by the pressure sensor 43 is within an appropriate range. Furthermore, when the controller 49 determines that the repulsive force is within the appropriate range, the controller 49 controls the light source device 7 so as to cause the light source device 7 to generate therapeutic light, thereby irradiating the biological tissue S with the therapeutic light. In contrast, if the controller 49 determines that the repulsive force is not within the appropriate range, the controller 49 does not cause the light source device 7 to generate therapeutic light.

According to this modification, the controller 49 automatically controls the light source device 7, so that the biological tissue S can be irradiated with therapeutic light in a state where the biological tissue S against which the pressing surface 23a of the pressing section 23 is pressed is reasonably thin and has a nearly uniform thickness. This makes it possible to perform light treatment on the lesion P in the biological tissue S while omitting a troublesome task for the user.

Although the embodiments of the present invention have been described in detail above with reference to the drawings, specific configurations are not limited to these embodiments and include design alterations so long as they do not depart from the scope of the invention. For example, the present invention is not limited to being applied to each of the embodiments described above, and may be applied to an embodiment obtained by appropriately combining these embodiments, without particular limitation.

As an alternative to each of the above-described embodiments in which the pressing surface 23a of the pressing section 23 is given an embossing treatment or a roughening treatment, for example, the pressing surface 23a may be a flat surface with no protrusions or recesses.

As an alternative to each of the above-described embodiments in which the endoscope insertion section 11 has the groove 11b and the endoscope hood 5 has the claw 27b, for example, the endoscope insertion section 11 may have a claw protruding radially outward from the outer peripheral surface of the distal end 11a, and the endoscope hood 5 may have a groove recessed radially outward in the inner peripheral surface of the engagement hole 27a. Furthermore, if the state where the distal end 11a of the endoscope insertion section 11 and the attachment section 27 of the endoscope hood 5 are attached to each other can be sufficiently maintained, the endoscope insertion section 11 and the endoscope hood 5 do not have to have the groove and the claw.

As an alternative to each of the above-described embodiments in which the endoscope hood 5 has the fiber insertion hole 29 in the main body 21, a configuration in which the main body 21 does not have the fiber insertion hole 29 is also possible. In this case, the distal end 13a of the optical fiber 13 does not protrude forward of the distal end 11a of the endoscope insertion section 11, and the main body 21 and the pressing section 23 of the endoscope hood 5 may both be formed of a component through which therapeutic light is transmittable.

In each of the above-described embodiments, the optical fiber 13 that outputs therapeutic light from the side surface of the distal end 13a is described as an example. Alternatively, for example, an optical fiber that outputs therapeutic light from the entire distal end 13a including the distal end surface 13b may be employed, or an optical fiber that outputs therapeutic light only from the distal end surface 13b of the distal end 13a may be employed.

The above-described embodiment also leads to the following aspects.

An aspect of the present invention provides an endoscope hood attached to an endoscope insertion section including an optical fiber that optically guides therapeutic light with which biological tissue is to be irradiated and outputs the therapeutic light from a distal end, and also including an observation optical system for observing the biological tissue. The endoscope hood includes an attachment section attached to a distal end of the endoscope insertion section, a pressing section disposed at a position where the pressing section covers the distal end of the optical fiber and including a pressing surface that presses against the biological tissue, and a light transmission section disposed forward of the observation optical system. The therapeutic light is transmittable through the pressing section. Light is transmittable through the light transmission section toward the observation optical system.

According to this aspect, in a state where the attachment section is attached to the distal end of the endoscope insertion section, the observation optical system is used to check the position of the biological tissue to be treated based on observation light incident thereon from the biological tissue via the light transmission section. Then, in a state where the pressing surface of the pressing section disposed at the position where the pressing surface covers the distal end of the optical fiber in the endoscope insertion section is pressed against the biological tissue to be treated, the therapeutic light optically guided by the optical fiber of the endoscope insertion section is output from the distal end of the optical fiber, so that the biological tissue to be treated is irradiated with the therapeutic light via the pressing surface of the pressing section.

In this case, the pressing surface of the pressing section is pressed against the biological tissue to be treated, so that the biological tissue to be treated can be reduced in thickness and can have a nearly uniform thickness. By outputting the therapeutic light in this state, a deep part of the biological tissue can be irradiated with a sufficient amount of therapeutic light more reliably.

The endoscope hood according to the above aspect may further include an insertion hole that extends toward the pressing surface from the attachment section and into which the distal end of the optical fiber is insertable.

According to this configuration, the distal end of the optical fiber in the endoscope insertion section is inserted into the insertion hole, so that the attachment section is positioned in the circumferential direction of the endoscope insertion section. Accordingly, the pressing surface of the pressing section can be disposed at the position where the pressing surface covers the distal end of the optical fiber, and the attachment section can be attached easily and accurately to the distal end of the endoscope insertion section in a position where the light transmission section is disposed forward of the observation optical system.

The endoscope hood according to the above aspect may further include an internal light blocking member disposed between a position where the distal end of the optical fiber is disposed and the light transmission section. The therapeutic light output from the distal end of the optical fiber is prevented from entering the light transmission section by the internal light blocking member.

According to this configuration, the internal light blocking member can prevent the therapeutic light output from the distal end of the optical fiber in the endoscope insertion section from entering the field of view of the endoscope insertion section via the light transmission section. Accordingly, the observation of the biological tissue to be treated using the observation optical system is prevented from being hindered by the therapeutic light, so that the biological tissue to be treated can be observed while light treatment is being performed thereon.

In the endoscope hood according to the above aspect, the light transmission section may include a filter member that blocks the therapeutic light incident thereon from the biological tissue.

According to this configuration, the filter member can prevent the therapeutic light output from the distal end of the optical fiber via the pressing surface of the pressing section, coming in from the biological tissue, and passing through the light transmission section from entering the observation optical system. Accordingly, the biological tissue can be observed more reliably and with higher accuracy while light treatment is being performed thereon.

In the endoscope hood according to the above aspect, the pressing surface may be given an embossing treatment or a roughening treatment.

According to this configuration, the friction between the biological tissue and the pressing surface of the pressing section can be increased. Accordingly, in a state where the pressing surface is pressed against the biological tissue, the pressing section is less likely to be positionally displaced relative to the biological tissue.

In the endoscope hood according to the above aspect, the pressing surface may have a shape surrounded by a circular-arc-shaped first outer peripheral portion serving as a part of a circumference around a central axis of the endoscope insertion section and by a second outer peripheral portion defined by a remaining part of the circumference being recessed radially inward into a shape of a circular arc. The first outer peripheral portion may have a curvature equal to a curvature of the second outer peripheral portion.

According to this configuration, in a case where the position where the pressing surface is pressed against the biological tissue is to be shifted sideways, the first outer peripheral portion of the pressing surface is aligned with the position corresponding to the second outer peripheral portion in the trace of the pressing surface in the biological tissue, whereby a gap between adjacent pressing locations can be reduced as much as possible. Accordingly, in a case where the biological tissue to be treated extends over a wide range, the biological tissue can be efficiently irradiated with the therapeutic light without waste while the pressing position of the pressing surface is shifted sideways.

In the endoscope hood according to the above aspect, the pressing surface may have a protruding shape protruding toward the biological tissue or a recessed shape recessed toward the endoscope insertion section.

According to this configuration, in a case where the surface of the biological tissue to be treated has a protruding shape or a recessed shape, the pressing surface of the pressing section can be brought into close contact with the surface of the biological tissue more easily.

In the endoscope hood according to the above aspect, the pressing section may be formed of a scattering element that scatters the therapeutic light.

According to this configuration, the therapeutic light output from the distal end of the optical fiber via the pressing section can be scattered, so that the biological tissue can be treated more efficiently over a wide range.

The endoscope hood according to the above aspect may further include an external light blocking member disposed at a position where the external light blocking member covers an overall side surface including the pressing section and the light transmission section. The therapeutic light is blocked by the external light blocking member.

According to this configuration, it is possible to prevent a portion of the therapeutic light output from the distal end of the optical fiber from being output outward from the overall side surface including the pressing section and the light transmission section. Accordingly, areas other than the biological tissue to be treated can be prevented from being irradiated with the therapeutic light.

In the endoscope hood according to the above aspect, the light transmission section may be composed of a transparent material, or the light transmission section may be a space formed by a partially cut-out region of the pressing section.

In the endoscope hood according to the above aspect, the attachment section may include a claw or a groove in an inner peripheral surface of the attachment section and may be engageable with the distal end of the endoscope insertion section by using the claw or the groove.

According to this configuration, the attachment section of the endoscope hood is engaged with the distal end of the endoscope insertion section by using the claw or the groove of the attachment section of the endoscope hood. Accordingly, when the pressing surface of the endoscope hood is pressed against the biological tissue, the endoscope hood is less likely to become detached from the distal end of the endoscope insertion section even if pressure is applied to the endoscope hood in a direction intersecting the longitudinal direction of the endoscope insertion section.

Another aspect of the present invention provides an endoscope system including an endoscope insertion section and the aforementioned endoscope hood attached to the endoscope insertion section.

According to this aspect, the endoscope hood is attached to the endoscope insertion section, and the pressing surface of the endoscope hood is pressed against the biological tissue to be treated, so that the biological tissue can be reduced in thickness and can have a nearly uniform thickness. In this state, the biological tissue is irradiated with the therapeutic light optically guided by the optical fiber of the endoscope insertion section via the pressing surface of the endoscope hood, so that a deep part of the biological tissue can be irradiated with a sufficient amount of therapeutic light more reliably.

The endoscope system according to the above aspect may further include a pressure sensor that measures a repulsive force from the biological tissue to the pressing surface of the endoscope hood, and a notification unit that provides a notification about information related to the repulsive force measured by the pressure sensor.

According to this configuration, when the pressing surface of the pressing section in the endoscope hood is pressed against the biological tissue in a state where the endoscope hood is attached to the endoscope insertion section, the pressure sensor measures the repulsive force from the biological tissue to the pressing surface of the endoscope hood, and the notification unit provides the notification about the information related to the measured repulsive force.

Accordingly, the user can irradiate the biological tissue with therapeutic light while ascertaining that the biological tissue against which the pressing surface of the pressing section is pressed is reasonably thin and has a nearly uniform thickness based on the notification information provided by the notification unit. Accordingly, a deep part of the biological tissue can be irradiated with a sufficient amount of therapeutic light more reliably, so that the biological tissue can be treated easily and efficiently.

REFERENCE SIGNS LIST 1, 41 endoscope system
5 endoscope hood
11 endoscope insertion section
13 optical fiber
23 pressing section
23a pressing surface
23b first outer peripheral portion
23c second outer peripheral portion
25 space section (light transmission section)
27 attachment section
27b claw
29 fiber insertion hole (insertion hole)
31 transparent section (light transmission section)
33 light blocking member (internal light blocking member)
35 filter (filter member)
37 light blocking member (external light blocking member)
43 pressure sensor
47 notifier (notification unit)
S biological tissue

The invention claimed is:

1. An endoscope hood for use with an endoscope, the endoscope hood comprising:
    a hood body comprising:
        a proximal portion configured to be attached to a distal end of the endoscope; and
        a distal portion comprising:
            a first longitudinal portion comprising a pressing surface on a distal face of the first longitudinal portion, the pressing surface being configured to press against biological tissue, therapeutic light being transmittable distally through the pressing surface; and
            a second longitudinal portion having a recessed surface recessed proximally from the distal face, observation light being transmittable proximally through the recessed surface; and
        an internal light blocking material disposed in the hood body between the first and second longitudinal portions, the light blocking material is configured to block the therapeutic light from passing to the second longitudinal portion from the first longitudinal portion.

2. The endoscope hood according to claim 1, further comprising an insertion hole extending longitudinally in the first longitudinal portion from the proximal portion and configured for insertion of a distal end of an optical fiber.

3. The endoscope hood according to claim 2, wherein the proximal portion has a first diameter, and
    the insertion hole has a second diameter smaller than the first diameter.

4. The endoscope hood according to claim 1, wherein the second longitudinal portion includes a filter member configured to block the therapeutic light incident on the recessed surface from biological tissue.

5. The endoscope hood according to claim 1, wherein the pressing surface is a rough surface.

6. The endoscope hood according to claim 1, wherein the pressing surface has an outer peripheral shape having a circular-arc-shaped first outer peripheral portion and a second outer peripheral portion defined by a transition between the pressing surface and the recessed surface.

7. The endoscope hood according to claim 6, wherein the first outer peripheral portion has a curvature equal to a curvature of the second outer peripheral portion.

8. The endoscope hood according to claim 1, wherein the pressing surface has a concavity recessed toward the proximal portion.

9. The endoscope hood according to claim 1, wherein the first longitudinal portion comprises a scattering element configured to scatter the therapeutic light.

10. The endoscope hood according to claim 1, further comprising an external light blocking material disposed at an overall side surface of the hood body, the external blocking material being configured to block the therapeutic light.

11. The endoscope hood according to claim 1, wherein the second longitudinal portion comprises a transparent material.

12. The endoscope hood according to claim 1, wherein the recessed surface forms a space at a distal portion of the second longitudinal portion.

13. The endoscope hood according to claim 1, wherein the proximal portion includes one of a claw or a groove in an inner peripheral surface of the proximal portion, the one of the claw or groove being configured to engage with an other of the claw or groove disposed at the distal end of the endoscope.

14. An endoscope system comprising:
    an endoscope insertion section;
    an optical fiber configured to output the therapeutic light from a distal end; and
    the endoscope hood according to claim 1 attached to the endoscope insertion section.

15. The endoscope system according to claim 14, further comprising:
    a pressure sensor configured to measure a repulsive force from the biological tissue to the pressing surface; and
    a processor configured to provide a notification about information related to the repulsive force measured by the pressure sensor.

16. The endoscope hood according to claim 14, wherein the pressing surface covers the distal end of the optical fiber.

17. The endoscope hood according to claim 1, wherein the distal face is a first distal face and the recessed surface is a second distal face disposed proximally relative to the first distal face.

18. The endoscope hood according to claim 17, wherein the first longitudinal portion has an insertion hole extending from the proximal portion toward the pressing surface, the insertion hole configured to receive a distal end of an optical fiber, a distal end of the hole is disposed between the pressing surface and the second distal face.

19. The endoscope hood according to claim 1, wherein
    the distal face is a first distal face and the recessed surface is a second distal face disposed proximally relative to the first distal face;
    the second longitudinal portion has a transparent section extending proximally from the second distal face; and the first longitudinal portion has an insertion hole extending from the proximal portion toward the pressing surface, the insertion hole configured to receive a distal end of an optical fiber.

20. The endoscope hood according to claim 19, wherein the internal light blocking material is disposed between the insertion hole and the transparent section.

\* \* \* \* \*